(12) United States Patent
Etoh et al.

(10) Patent No.: US 6,696,266 B1
(45) Date of Patent: *Feb. 24, 2004

(54) METHOD FOR ASSAYING AMMONIA USING AN NAD-BASED CYCLING REACTION SYSTEM

(75) Inventors: Takashi Etoh, Shizuoka (JP); Mamoru Takahashi, Shizuoka (JP)

(73) Assignee: Asahi Kasei Pharma Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 388 days.

(21) Appl. No.: 09/101,695
(22) PCT Filed: Jan. 17, 1997
(86) PCT No.: PCT/JP97/00080
§ 371 (c)(1), (2), (4) Date: Sep. 17, 1998
(87) PCT Pub. No.: WO97/29208
PCT Pub. Date: Aug. 14, 1997

(30) Foreign Application Priority Data

Feb. 9, 1956 (JP) ................................. 8/23564

(51) Int. Cl.⁷ ................................................. C12Q 1/32
(52) U.S. Cl. ........................................................ 435/26
(58) Field of Search ............................ 435/26, 15, 16, 435/28

(56) References Cited

U.S. PATENT DOCUMENTS

| | | | |
|---|---|---|---|
| 4,767,712 A | 8/1988 | Misaki et al. | |
| 4,921,786 A | 5/1990 | Takahashi et al. | |
| 5,206,146 A | * 4/1993 | Misaki et al. | ................. 435/16 |

FOREIGN PATENT DOCUMENTS

| | | | |
|---|---|---|---|
| EP | 0 260 137 | | 3/1988 |
| JP | 1-191698 | * | 8/1989 |

OTHER PUBLICATIONS

Sung H. Determination of Microquantities of Ammonia by Enzymatic Analysis. Korean J Applied Microbiology Bioengineering. 14(6)495–500, 1986.*

Zalkin H., "NAD Synthetase", Methods in Enzymology, vol. 113, 1985, XP009007324, pp. 297–302.

R.L. Spencer et al., "Biosynthesis of Diphosphopyridine Nucleotide", pp. 385–392, The Journal of Biological Chemistry, vol. 242, No. 3, Feb. 10, 1967.

* cited by examiner

*Primary Examiner*—Ralph Gitomer
(74) *Attorney, Agent, or Firm*—Young & Thompson

(57) ABSTRACT

A method for assaying ammonia and/or ammonium ions contained in a liquid sample which comprises subjecting the sample to a reaction at least in the presence of an NAD synthetase, deamidated NAD, ATP, $Mg^{2+}$ ions and/or $Mn^{2+}$ ions, a dehydrogenase capable of forming ammonia molecules from an amine substrate and an oxidized NAD, and the amine substrate, and then determining the amounts of the ingredients consumed or generated by the reaction; and an assaying composition comprising all of the above-specified ingredients. The method is inexpensive and is effective in accurately assaying ammonia and/or ammonium ions present in a few minutes.

7 Claims, 8 Drawing Sheets

METHOD FOR ASSAYING AMMONIA USING AN NAD-BASED CYCLING REACTION SYSTEM

CROSS REFERENCE TO RELATED APPLICATION

This is the 35 USC 371 national stage of international application PCT/JP97/00080 filed on Jan. 17, 1997, which designated the United States of America which claims priority to JAPAN 8-23564 filed Feb. 9, 1996.

FIELD OF THE INVENTION

This invention relates to an assaying composition for high sensitive assay of a small amouunt of ammonia and/or ammonium ions using NAD synthetase. More particularly the present invention relates to a method for assaying ammonia and/or ammonium ions contained in a liquid sample which comprises subjecting the sample to a reaction in the presence of an NAD synthetase, deamidated NAD, ATP, $Mg^{2+}$ ions and/or $Mn^{2+}$ ions, a dehydrogenase capable of forming ammonia molecules from an amine substrate and an oxidized NAD, and the amine substrate, and then determining the amounts of the components consumed or generated by the reaction. The present invention further relates to an assaying composition for ammonia and/or ammonium ions comprising containing NAD synthetase, deamidated NAD, ATP, $Mg^{2+}$ ions and/or $Mn^{2+}$ ions, a dehydrogenase capable of forming ammonia molecules from an amine substrate and oxidized NAD, and the amine substrate.

BACKGROUND OF THE INVENTION

Ammonia and/or ammonium ions are generated during protein metabolism in vivo and are used for biosynthesis of other nitrogen compounds in the liver. Excess ammonia and/or ammonium ions are excreted in urine after synthesis of urea. If the liver is injured or fails, abnormal ammonia metabolism will occur and high level of ammonia and/or ammonium ions in blood will be observed. Consequently, assaying ammonia and/or ammonium ions in blood is an indicator of the liver failure. Prior known assay methods of ammonia and/or ammonium ions are not sufficiently sensitive and thus cause erroneous measurements.

Creatinine is important in the diagnosis of renal functions, however prior known assay have low sensitivity which results in incomplete diagnosis.

Hitherto known assay methods of ammonia and/or ammonium ions using NAD synthetase (EC 6. 3. 1. 5 and EC 6. 3. 5. 1) are: a method assaying directly a reduced NAD using oxidoreductase and its substrates from oxidized NAD generated by enzymatic action of NAD synthetase; a method for measuring a small amount of ammonia by colored formazan with diaphorase and tetrazolium salt in a reaction mixture; and a method for measuring generated colored hydrogen peroxide by combination of oxidase system therewith. The reaction systems are illustrated as follows. (Japanese Patent Unexamined Publication No. 59-198995, U.S. Pat. No. 4,767,712, ibid. U.S. Pat. No. 5,206,146, Japan Pat. Unexam. Publ. No.63-185378 and U.S. Pat. No. 4,921.786). In these reaction systems, neither P1 (oxidized product of S1) nor P3 (oxidized product of S3) reaction product generate the cycling reaction.

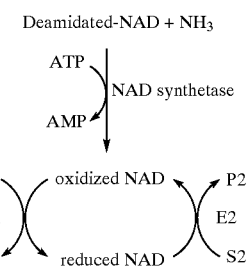

wherein:
E1: dehydrogenase which catalyzes a reaction with consuming oxidized NAD and substrate S1, while generating reduced NAD and P1.
E2: active substance which catalyzes a reaction with consuming reduced NAD and S2, while generating oxidized NAD and P2.
S1: reduced substrate of E1.
S2: oxidized substrate of E2.
P1: oxidized substrate of S1.
P2: reduced substrate of S2.

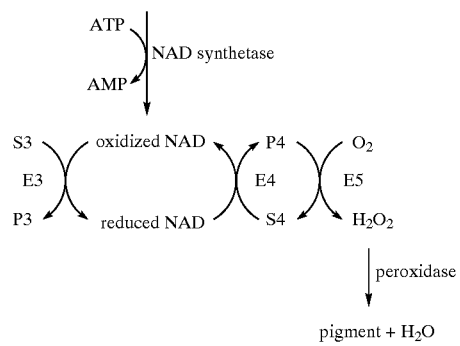

wherein:
E3: dehydrogenase which catalyzes a reaction with consuming coenzyme oxidized NAD and substrate S3, while generating reduced NAD and P3.
E4: active substance which catalyzes a reaction with consuming coenzyme reduced NAD and substrate S4, while generating oxidized NAD and P4.
E5: oxidase which catalyzes a reaction with oxidizing P4 by enzymatic action while generating hydrogen peroxide and S4.
S3: reduced substrate of E3.
S4: oxidized substrate of E4.
P3: oxidized substrate of S3.
P4: oxidized substrate of S4.

In assaying a small amount of ammonia or ammonium generated from decomposed creatinine by an action of creatinine deiminase in the assay of creatinine in a specimen, direct assay of reduced NAD has a problem due to lower sensitivity, and the method with assaying formazan is highly sensitive but has an adsorption problem of pigment to an equipment. Further, oxidase system is easily affected by reduced substance such as ascorbic acid and has turned out to be expensive due to the use of a number of enzymes.

Accurately assaying ammonium and/or ammonium ions present in minute amounts has been difficult until now.

Consequently, there is a need for an inexpensive and high sensitive assay method and an assaying composition.

SUMMARY OF THE INVENTION

We have tried to solve the above problems in assaying a small amount of ammonia and/or ammonium ions by using NAD synthetase, and made efforts to find a highly sensitive assaying method. Namely, ammonia and/or ammonium ions and a deamidated-NAD are reacted by an action of NAD synthetase in the presence of ATP, $Mg^{2+}$ ions and/or $Mn^{2+}$ ions, under the combination of a dehydrogenase capable of forming ammonia molecules from an amine substrate and an oxdized NAD, such as L-amino acids dehydrogenase and D-amino acids dehydrogenase, with the amine substrate, to form AMP and oxidized NAD. The thus formed oxidized-NAD is reacted with the amine substrates by an action of a dehydrogenase capable of forming ammonia molecules from an amine substrate and an oxidized NAD, to construct ammonia cycling and form the oxidized substrate and ammonia and/or ammonium ions. The thus accumulated reduced NAD is directly or continuously measured, or the oxidized substrate formed from the substrate accompanied by the formation of reduced NAD is measured continuously, to successfully measure ammonia and/or ammonium ions with high sensitivity. The present invention was completed by finding the above method.

An object of the present invention is to provide a method for assaying ammonia and/or ammonium ions contained in a liquid sample which comprises subjecting the sample to a reaction in the presence of an NAD synthetase, deamidated-NAD, ATP, $Mg^{2+}$ ions and/or $Mn^{2+}$ ions, a dehydrogenase capable of forming ammonia molecules from an amine substrate and an oxidized NAD, and the amine substrate, and then determining the amounts of the components consumed or generated by the reaction.

Another object of the present invention is to provide an assaying composition for ammonia and/or ammonium ions comprising containing NAD synthetase, deamidated NAD, ATP, $Mg^{2+}$ ions and/or $Mn^{2+}$ ions, a dehydrogenase capable of forming ammonia molecules from an amine substrate and an oxidized NAD, and amine substrate.

The present invention is explained in details as follows.

A reaction system of the present invention is summarized as follows.

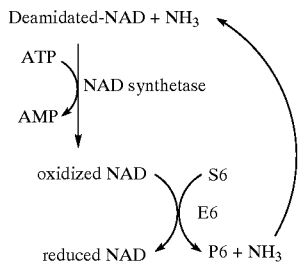

wherein:

E6: dehydrogenase which catalyzes a reaction generating reduced NAD, and P6 and ammonia molecules from substrate S6, and coenzyme oxidized NAD.

S6: reduced substrate of E6.

P6: oxidized product of S6.

Liquid samples or specimens of the present invention can be the samples containing ammonia (including ammonium ions), further the samples containing ammonia liberated or generated from the other enzyme reactions, which can be liberated or generated ammonia, or liberated or generated from acid or alkaline hydrolysis system, for example specimens such as blood, serum and urine. Examples of the above enzyme reaction systems can be any enzyme systems generating ammonia. Examples of enzyme reaction systems, in which their enzyme actions or substrates involved in these reactions are measured, are illustrated as follows.

(1) creatinine deiminase (EC 3. 5. 4. 21)

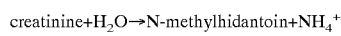

(2) guanine deaminase (EC 3. 5. 4. 3)

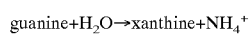

(3) adenosine deaminase (EC 3. 5. 4. 4)

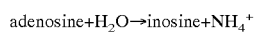

Examples of a dehydrogenase capable of forming ammonia molecules from an amine substrate and an oxidized NAD, and the amine substrate are preferably L-amino acids dehydrogenase and its substrates. Any L-amino acids dehydrogenase, which uses coenzyme oxidized NAD formed by enzymatic reaction of NAD synthetase and substrate L-amino acids, and forms 2-oxo acids and ammonia from L-amino acids, can be used without limitation. Examples of enzymes and substrates will be illustrated hereinbelow and are enzymes and substrates such as amine substrate including L-amino acids, D-amino acids and diamines. These can be used in any number of single or multiples. As examples, following L-amino acids dehydrogenase and their substrates can be mentioned.

It should be noted that NAD synthetase (Japan. Pat. Unexam. Publ. No. 63-185378 and U.S. Pat. No. 4,921,786) [*Bacillus stearothermophilus* H-804: FERM BP-1408 and FERM BP-5381 (These were deposited in the National Institute of Bioscience and Human-Technology, Agency of Industrial Science and Technology, Ministry of International Trade and Industry, in 1-1-3, Higash, Tsukuba-shin, Ibaragi-ken, Japan, by the depositor: Asahi Kasei Kogyo Kabushiki Kaisha, 1-2-6, Dojimahama, Kita-ku, Osaka-shi, Osaka)] is specified as not using glutamine and aspargine as amino donor. Consequently, the strain can use all of the illustrated dehydrogenase capable of forming ammonia molecules from an amine substrate and an oxidized NAD. However, there are NAD synthetase which can use glutamine and asparagine (Spencer, R. L., J. Biol. Chem., 242, 285–392, 1967).

If the latter NAD synthetase is used, a dehydrogenase capable of forming ammonia molecules from the amine substrate and the oxidized NAD, which does not use at least glutamine or aspargine as an amino donor, should be used.

Examples of enzyme reactions are illustrated hereinbelow, but are not limited to the present invention, since, in some cases, the enzyme activity for substrate specificity is quite low.

(4) L-alanine dehydrogenase (EC 1. 4. 1. 1)

L-alanine+$H_2O$+oxidized NAD⇌pyruvate+ammonia+reduced NAD (5) L-glutamate dehydrogenase (EC 1. 4. 1. 2)

L-glutamate+$H_2O$+oxidized NAD⇌2-oxoglutarate+ammonia +reduced NAD (6) L-serine dehydrogenase (EC 1. 4. 1. 7)

L-serine+$H_2O$+oxidized NAD→hydroxypyruvate+ammonia+reduced NAD (7) L-valine dehydrogenase (EC 1. 4. 1. 8)

L-valine+$H_2O$+oxidized NAD→2-oxoisovalerate+ammonia+reduced NAD (8) L-leucine dehydrogenase (EC 1. 4. 1. 9)

L-leucine+$H_2O$+oxidized NAD→2-oxoisocaproate+ammonia+reduced NAD (9) glycine dehydrogenase (EC 1. 4. 1. 10)

glycine+$H_2O$+oxidized NAD→glyoxylate+ammonia+reduced NAD

(10) L-amino acid dehydrogenase (EC 1. 4. 1. 5)

L-amino acid+$H_2O$+oxidized NAD→2-oxo acid+ammonia+reduced NAD

(11) L-erythro 3,5-diaminohexanoate dehydrogenase (EC 1. 4. 1. 11)

L-erythro-3,5-diaminohexanoate+$H_2O$+oxidized NAD→5-amino-3-oxo-hexanoate+ammonia+reduced NAD

(12) 2,4-diaminopentanoate dehydrogenase (EC 1. 4. 1. 12)

2,4-diaminopentanoate+$H_2O$+oxidized NAD→2-amino-4-oxanopentanoate+ammonia+reduced NAD

(13) L-lysine dehydrogenase (EC 1. 4. 1. 15)

L-lysine+$H_2O$+oxidized NAD→1,2-didehydropiperidine-2-carboxylate+ammonia+reduced NAD

(14) L-tryptophane dehydrogenase (EC 1. 4. 1. 19)

L-tryptophane+$H_2O$+oxidized NAD→(indol-3-yl) pyruvate+ammonia+reduced NAD

(15) L-phenylalanine dehydrogenase (EC 1. 4. 1. 20)

L-phenylalanine+$H_2O$+oxidized NAD phenylpyruvate+ammonia+reduced NAD

(16) D-amino acid dehydrogenase

D-amino acid+$H_2O$+oxidized NAD→2-oxo acid+ammonia+reduced NAD

(17) D-alanine dehydrogenase

D-alanine+$H_2O$+oxidized NAD→pyruvate+ammonia+reduced NAD

(18) D-phenylalanine dehydrogenase

D-phenylalanine+$H_2O$+oxidized NAD phenylpyruvate+ammonia+reduced NAD

(19) D-phenylserine dehydrogenase

D-threo-3-phenylserine+$H_2O$+oxidized NAD→D-2-amino-3-keto-3-phenylpropionate+ammonia+reduced NAD

(20) D-tryptophane dehydrogenase

D-tryptophane+$H_2O$+oxidized NAD→(indol-3-yl) pyruvate+ammonia+reduced NAD

(21) D-lysine dehydrogenase

D-lysine+$H_2O$+oxidized NAD→1,2-didehydropiperidine-2-carboxylate+ammonia+reduced NAD Examples of L-amino acid in the above reaction (10) are, for example, L-alanine, L-serine, L-valine, L-leucine and L-isoleucine. 2-oxo acid in the reaction means oxo acid formed L-amino acid. The above reactions (4)–(10) and (13)–(15) are L-amino acids dehydrogenases; the reactions (11)–(12) are diamine dehydrogenases; and the reactions (16)–(21) are D-amino acid dehydrogenases. These are involved in dehydrogenase capable of forming ammonia molecules from oxidized NAD and amine substrates of L-amino acids, diamine and D-amino acid. In the present invention, these types of enzyme are in any event included.

In the practice of the present invention, concentration of each reagent in the composition for measurement of trace amount of ammonia (including ammonium ions) can be an excess amount showing maximum reaction rate. A concentration of deamidate NAD is, for example, 0.01 mM–100 mM, preferably 0.1–5 mM. A concentration of ATP is, for example, 0.01–200 mM, preferably 0.5–20 mM. A concentration of $Mg^{2+}$ is, for example, 0.01–200 mM, preferably 0.5–20 mM as magnesium chloride or manganese chloride. A concentration of dehydrogenase capable of forming ammonia molecules from an amine substrate and an oxidized NAD is, for example, 0.05–1000 u/ml, preferably 1–250 u/ml. A concentration of amine substrate, which is a substrate of dehydrogenase capable of forming ammonia molecules from an amine substrate and an oxidized NAD, for example L-amino acids, which are substrate of L-amino acids dehydrogenases, is 0.05–250 mM, preferably 0.5–50 mM. A concentration of NAD synthetase is, for example, 0.1–100 u/ml, preferably 0.2–20 u/ml.

Reaction temperatures are usually 10–50° C., preferably 15° C.–50° C., preferably 15° C.–40° C. Reaction times are 1 min.–12 hours, preferably 1 min.–1 hour, and more preferably 1 min.–15 min. These values are not intended to limit the present invention.

According to the method of the present invention as illustrated in the following reaction scheme, ammonia (including ammonium ions, hereinafter sometimes simply designated as ammonia) can be assayed with high sensitivity and simply by measuring generated component by the reaction such as accumulated reduced NAD.

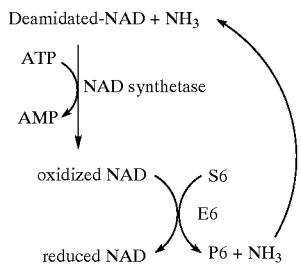

wherein:
E6: dehydrogenase which catalyzes a reaction generating reduced NAD, and P6 and ammonia molecules from substrate S6, and coenzyme oxidized NAD.
S6: reduced substrate of E6.
P6: oxidized product of S6.

In this reaction, a consumed or a generated component is measured. For example, a measurement of generated components includes measurement of reduced NAD generated by oxidative reaction of dehydrogenase capable of forming ammonia molecules from an amine substrate and an oxidized NAD. Further, for example, a measurement of generated component includes measurement of reduced NAD generated as a result of cycling reaction of ammonia which is newly generated by oxidative reaction of dehydrogenase capable of forming ammonia molecules from amine substrates and oxidized NAD.

A measurement of reduced NAD can be performed simply by measuring optical absorption at maximum absorption of reduced NAD at 340 nm. In lieu of the measurement by optical absorption, a measurement method can be taken by generating pigment such as formazan pigment by an action of enzyme such as diaphorase in the presense of chromogen and hydrogen acceptor, and measuring an amount of formazan pigment by means of increased absorption at maximum absorption such as 550 nm. Examples of hydrogen acceptor are methylene blue or tetrazolium salt such as known acceptor nitrotetrazolium blue (NTB). These are commercially available. Measurement can be performed, for example, by using prior known formazan coloring reaction using substrate 0.001–0.1% of nitrotetrazolium blue and diaphorase 0.01–500 u/ml, preferably 0.1–50 u/ml.

An assay can be performed by oxidized substrate of amine substrate generated by oxidative reaction of dehydrogenase capable of forming ammonia molecules from amine substrates and oxidized NAD. In the measurement of the oxidized substrate, a measurement means for measuring generated hydrogen peroxide or consumed oxygen using oxidase, which catalyzes a reaction consuming oxygen and generates hydrogen peroxide, with the said oxidized substrate, can be mentioned.

Relationships among the dehydrogenase capable of forming ammonia molecules from amine substrate and oxidized NAD, the amine substrate and the oxidized substrate are illustrated in the reactions (4)–(21) hereinbefore.

In the measurement of the oxidized substrate in the reaction (4) hereinbefore, for example, assay of pyruvate can be performed by using pyruvate oxidase, which catalyzes a reaction at least consuming oxygen and generating hydrogen peroxide, according to the following equation.

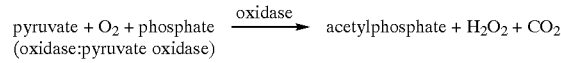
(oxidase:pyruvate oxidase)

For example, pyruvate generated by an action of alanine dehydrogenase can be measured according to the following reaction scheme by using pyruvate oxidase and peroxidase:

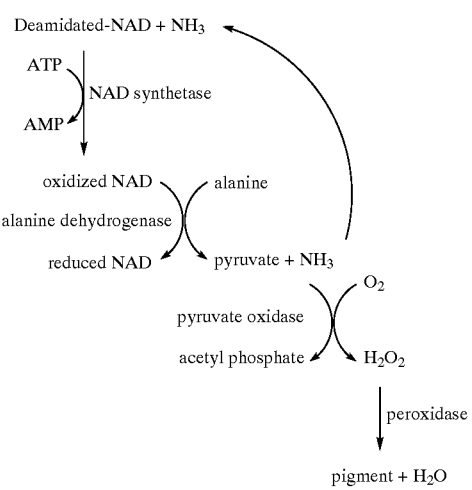

In this reaction, consumed oxygen or generated hydrogen peroxide can be simply measured.

Ammonia, contained in a liquid sample in this reaction can be the ammonia which said previously existed in the said liquid sample, or can be the liberated or the generated ammonia for assaying substrate or enzyme activity shown in the reactions (1)–(3) hereinbefore capable of liberating ammonia as a result of different reactions in accordance with present invention. A preferred example is a composition for assaying creatinine in a liquid sample containing creatinine deiminase, which can liberate or generate ammonia from creatinine. The liberated or generated ammonia from creatinine by the action of the creatinine deiminase can be assayed.

The above reaction is exemplified in the assay of pyruvate as the oxidized substrate by using L-alanine dehydrogenase (EC 1. 4. 1. 1) and its substrate L-alanine. As illustrated in the reactions (4)–(21) hereinbefore, L-alanine dehydrogenase (EC 1. 4. 1. 1) and its substrate can be, replaced as follows.

L-glutamate dehydrogenase (EC 1. 4. 1. 2), L-glutamate and oxidized substrate 2-oxo-glutarate;

L-serine dehydrogenase (EC 1. 4. 1. 7), L-serine and oxidized substrate hydroxypyruvate;

L-valine dehydrogenase (EC 1. 4. 1. 8), L-valine and oxidized substrate 2-oxo-isovalerate;

L-leucine dehydrogenase (EC 1. 4. 1. 9), L-leucine and oxidized substrate 2-oxo-isocapronate;

glycine dehydrogenase (EC 1. 4 .1. 10), glycine and oxidized substrate glyoxylate;

L-amino acid dehydrogenase (EC 1. 4. 1. 5), L-amino acid and oxidized substrate 2-oxo acids;

L-lysine dehydrogenase (EC 1. 4. 1. 15), L-lysine and oxidized substrate 1, 2-didehydropyperidino-2-carboxylate;

L-tryptophane dehydrogenase (EC 1. 4. 1. 19), L-tryptophane and oxidized substrate (indol-3-yl) pyruvate; and L-phenylalanine dehydrogenase (EC 1. 4. 1. 20), L-phenylalanine and oxidized substrate phenylpyruvate.

These substrates or consumed component oxygen or generated component hydrogen peroxide, can be measured.

Measurement oxygen can be performed by using an oxygen electrode.

In a measurement of hydrogen peroxide, the measurement can be performed by using hydrogen peroxide electrode or by using indicator which can change detectable product as a result of reaction with hydrogen peroxide. An indicator composition includes color reagent composition, which can show visible changes of color, fluorescent composition which can luminate by ultraviolet irradiation and color luminescent composition. These compositions can be used by measuring photometrically in their maximum absorbancy.

An example of color composition is usually a combination of a substance having peroxidase activity and coloring reagents. Example of a peroxidase active substance is horse raddish peroxidase and is used usually at 0.05–100 u/ml, preferably at 0.1–20 u/ml.

Coloring reagents are usually a combination of electron acceptor and phenol derivatives or aniline derivatives. Examples of electron acceptor are aminoantipyrine, 4-amino-3-hydrazino-5-mercapto-1,2,4-triazol, 2-hydradinobenzo thiazole. 3-methyl-2-benzothiazolone hydrazine and 2-amino-benzothiazol. 4-aminoantipyrine can be used at 0.01–15 mM, preferably 0.1–5 mM.

Examples of phenol derivatives are phenol, sodium p-hydroxy-benzonate, p-chlorophenol, 2,4-dichlorophenol, 4,6-dichloro-o-crezol, 2,4-dibromphenol, sodium 3,5-dichloro-2-hydroxybenzene sulfonate, and 3,5-oxylenol. Phenol is used usually at 0.001–0.2%, preferably 0.005–0.1%.

Examples of aniline derivatives are:

3-methyl-N-ethyl-N-(β-hydroxyethyl) aniline, N,N-dimethylaniline, N,N-diethylaniline, N,N-diethyl-m-toluidine, N,N-diethanol-m-toluidine, N,N-dimethyl-m-methoxyaniline, sodium N-ethyl-N-sulfopronyl-m-toluidine, N-ethyl-N-(3-methylphenyl)-N'-acetylethylenediamine, 3-acetamino-N,N-diethylaniline, N-ethyl-N-sulfopropyl-m-anisidine, N-ethyl-N-sulfopropylaniline, N-ethyl-N-sulfopropyl-3,5-dimethoxyaniline, N-sulfopropyl-3,5-dimethyoxyaniline, N-ethyl-N-sulfopropyl-3,5-dimethylaniline, N-ethyl-N-(2-hydroxy-3-sulfopropyl)-m-anisidine, N-ethyl-N-(2-hydroxy-3-sulfopropyl) aniline, N-ethyl-N-(2-hydroxy-3-sulfopropyl)-3,5-dimethoxyaniline, N-(2-hydroxy-3-sulfopropyl)-3,5-dimethoxyaniline, N-ethyl-N-(2-hydroxy-3-sulfopropyl)-3,5-dimethylaniline, and N-sulfopropylaniline.

For example, N-ethyl-N-(2-hydroxy-3-sulfopropyl)-3,5-dimethoxyaniline is used usually at 0.05–10 mM, preferably at 0.1–2 mM.

As luminescent substrate in the fluorescent composition or luminescent composition can be mentioned a known compounds. For example, these include 2,4,6-trichlorophenol, oxalate, phenylthiohidantoin, homovanillinic acid, 4-hydroxyphenylacetic acid, vanillylamine, 3-methoxytyramine, phloretin, hordenine, luminolmonoanion, acrydium ester, lumigenine and roffin. To obtain luminescence by an action of chemical luminescent reaction, catalysts which stimulate decomposition of hydrogen peroxide, such as $K_2S_2O_2$. NaClO, Fe (II) salt, Mn (II) salt, $NH_3$—$Cu^{2+}$, $K_3Fe (CN)_6$, Co (II) amine complex, hemoglobin, hemine and peroxidase, can be used. In the luminescent reaction, fluorescent substance may coexist to increase detection sensitivity, and simultaneously luminescent wave length can be changed to fluorescent wave length. Preferable fluorescent agents are 2-methylumbelliferone, fluoresceine and 9,10-diphenyl anthrascen.

In the assay of the above, rate assay, end-point assay or combination thereof can be selected. The reaction can be sent up as a one-step or two step reactions. Reagents can be selected either by using one reagent or 2 reagents with plural compositions.

DESCRIPTION OF THE PREFERRED EMBODIMENTS

The following examples illustrate the present invention, but are not to be construed as limiting the present invention.

EXAMPLE 1

A reaction mixture containing 40 mM potassium phosphate buffer (pH 7.0), 1 mM deamidated-$NAD^+$, 5 mM ATP, 5 mM magnesium chloride, 50 mM L-alanine, 50 u/ml L-alanine dehydrogenase (Asahi Chemical Industry Co.), and 1 u/ml NAD synthetase (originated from Bacillus stearothermophilus H-804: FERM BP-5381, Asahi Chemical Industry Co. hereinafter means the same origin of bacteria) was prepared. Reagent solutions, each consisting of ammonium chloride 0, 20, 40, 60, 80 and 100 µg/dl, respectively, were prepared. 30 µl of each reagent solution were added to 1 ml of reaction mixture. The reaction was started at 37° C.

Figure 1:
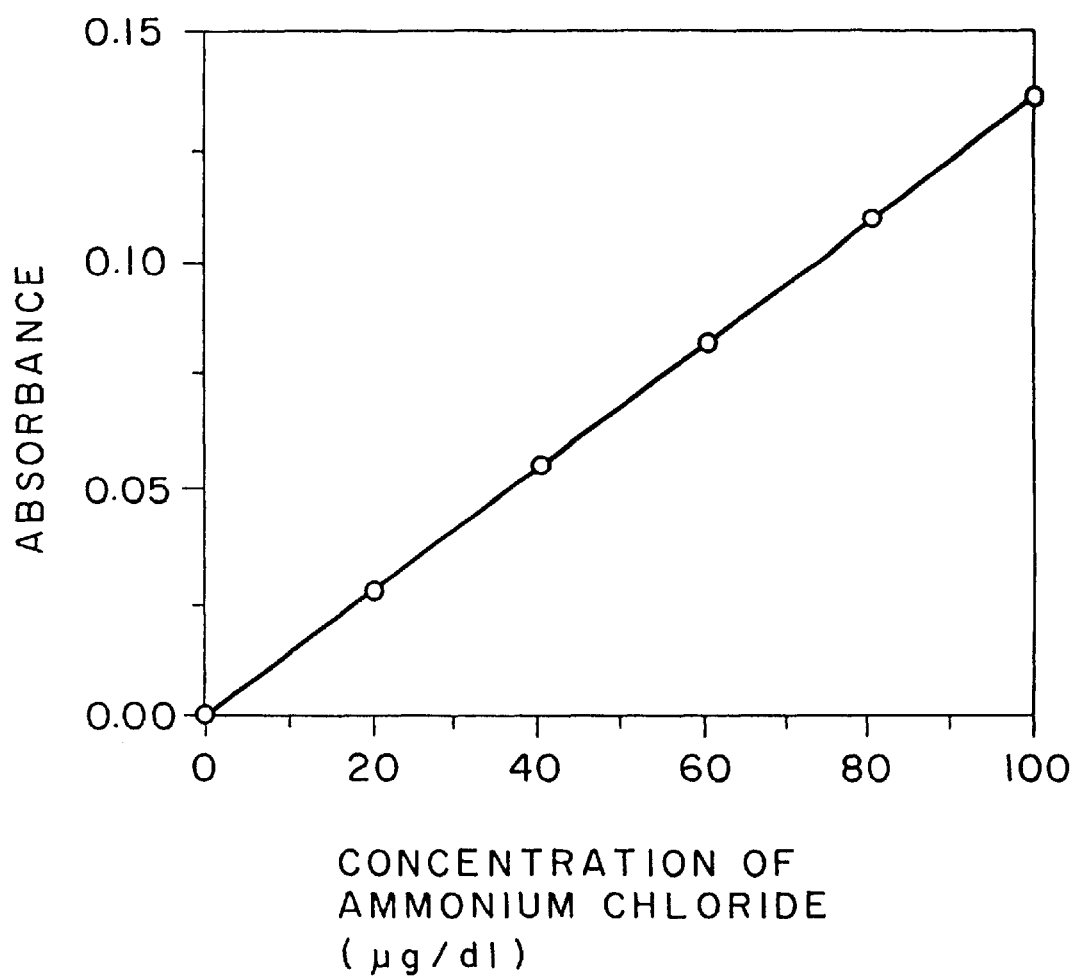
FIG. 1: A calibration curve for ammonia using assaying reagent containing L-alanine dehydrogenase.

Absorbance at 340 nm in each reaction mixture was measured for 5 minutes from 2 minutes to 7 minutes of the start by using 9 spectrophotometer. Result, which is detected concentration of ammonium chloride 0 as a blank, is shown in FIG. 1. As shown in FIG. 1, a quantitative assay of up to 100 μg/dl of ammonium chroride concentration is possible. It could be found that even at a concentration of 5 μg/dl, the method of the present invention had measurable sensitivity.

The data shown is a result of 10 cycling reactions/min. and if the amount of NAD synthetase is increased, the number of cyclings can be increased.

EXAMPLE 2

Figure 2:
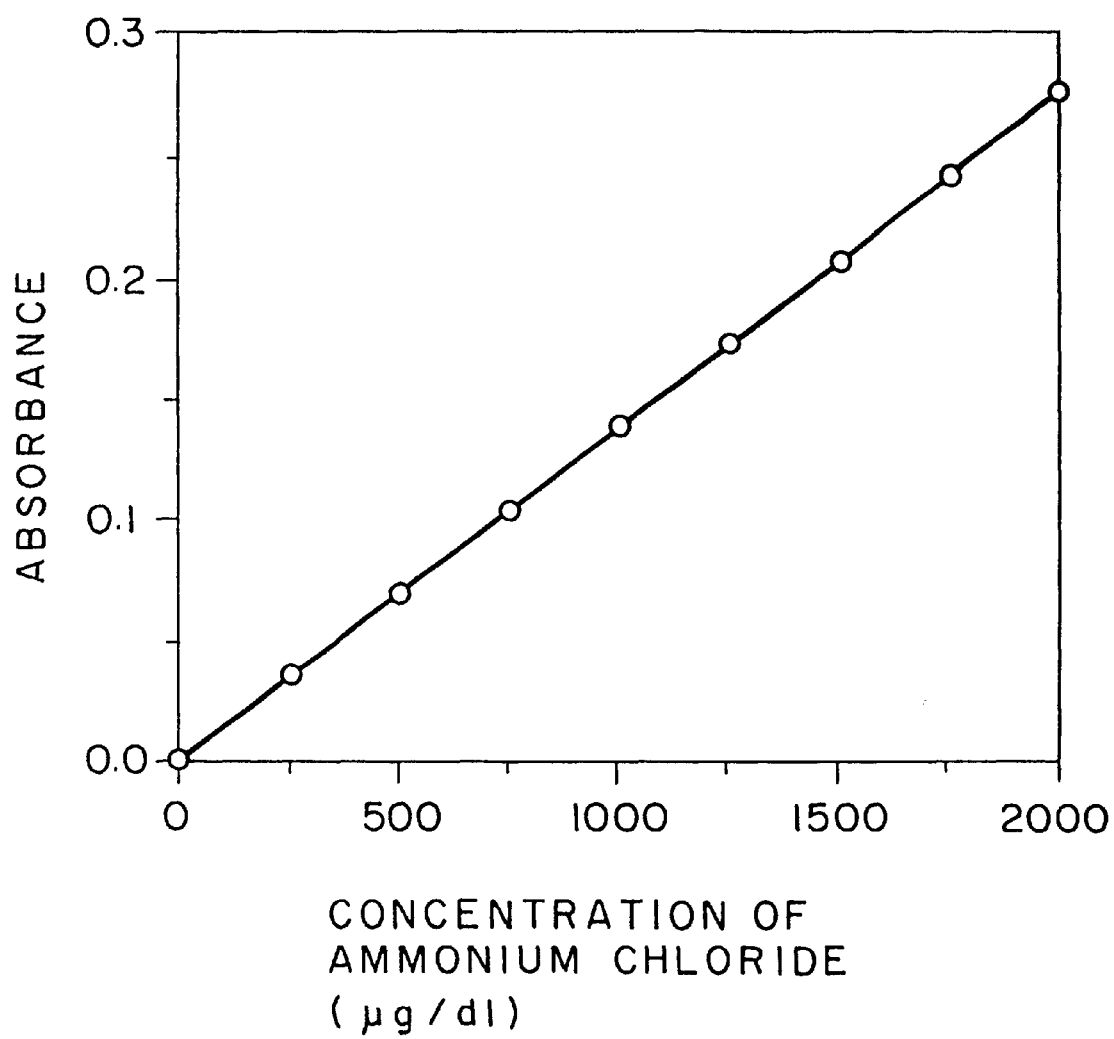
FIG. 2: A calibration curve for ammonia using assaying reagent containing L-alanine dehydrogenase.

A reaction mixture of the same composition as in example 1 was prepared. 5 μl of a reagent solution having ammonium chloride concentrations of 0, 250, 500, 750, 1000, 1250, 1500, 1750 and 2000 μg/dl, respectively, were added to 1 ml of the reaction mixture, and the reaction was started at 37° C. During 1 minute from 2 minute to 3 minute after the start, absorbancy at 340 nm was measured by using a spectrophotometer. Result, which is a detected value of ammonium concentration 0 as a blank, is shown in FIG. 2, in which a quantitative assay up to 2000 μg/dl of ammonium chloride is possible.

EXAMPLE 3

A reaction mixture containing 40 mM potassium phosphate buffer (pH 7.0), 1 mM deamidated $NAD^+$, 5 mM ATP, 5 mM magnesium chloride, 10 mM L-glutamic acid, 20 u/ml L-glutamate dehydrogenase (Sigma Inc.), and 1 u/ml NAD synthetase (Asahi Chemical Industry Co.) was prepared. Reagent solutions, each consisting of ammonium chloride 0, 20, 40, 60, 80 and 100 μg/dl, respectively, were prepared. 30 μl of each reagent solution were added to 1 ml of the reaction mixture. The reaction was started at 37° C.

Figure 3:
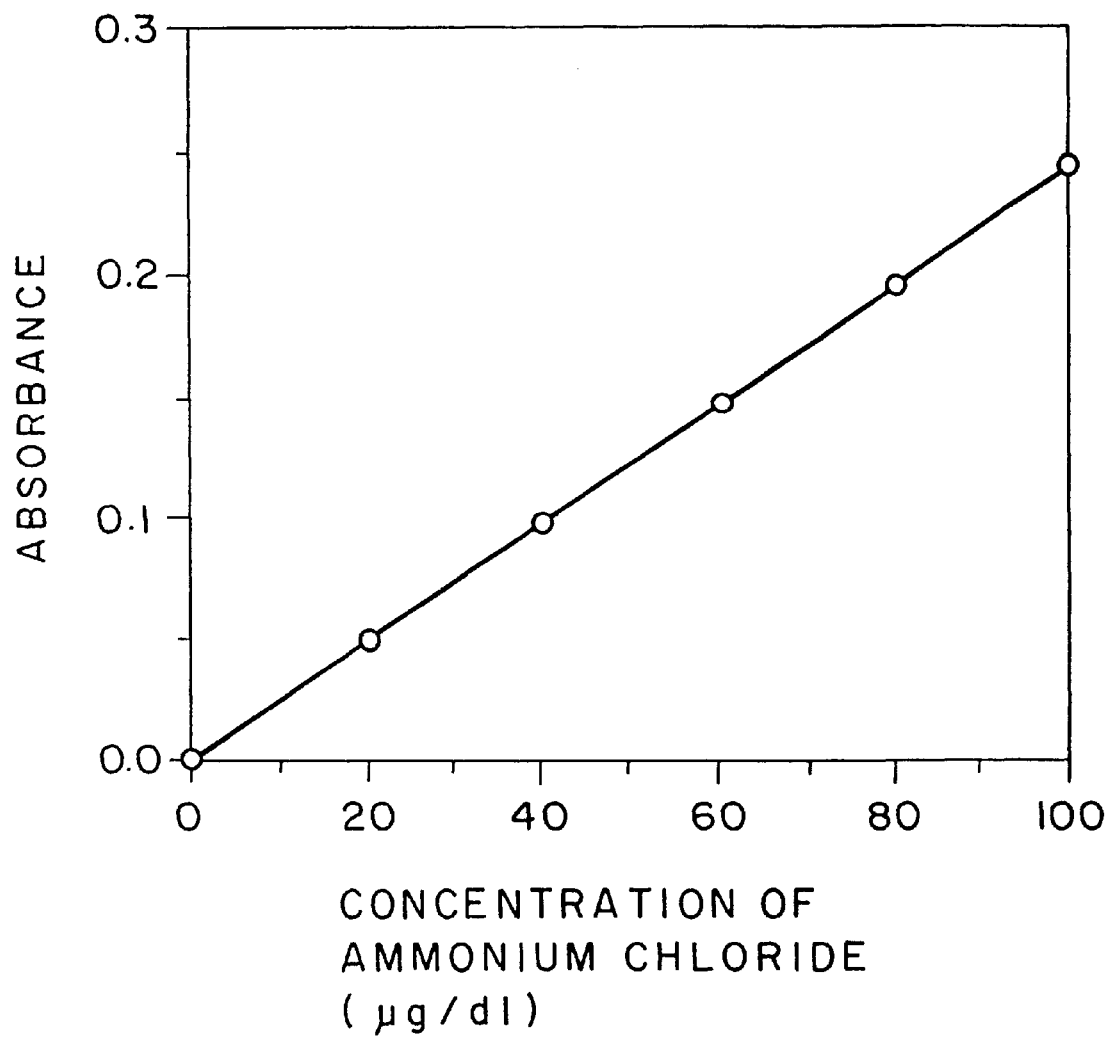
FIG. 3: A calibration curve for ammonia using assaying reagent containing L-glutamate dehydrogenase.

Absorbance at 340 nm in each reaction mixture was measured for 5 minutes from 2 minutes to 7 minutes of the start by using a spectrophotometer. Result, which is detected concentration of ammonium chloride 0 as a blank, is shown in FIG. 3. As shown in FIG. 3, a quantitative assay can of up to 100 μg/dl of ammonium chloride concentration is possible. It could be found that even at a concentration of 5 μg/dl, the method of the present invention had advantageous sensitivity.

EXAMPLE 4

A reaction mixture containing 40 mM potassium phosphate buffer (pH 8.0), 1 mM deamidated $NAD^+$, 5 mM ATP, 5 mM magnesium chloride, 10 mM L-leucine, 5 u/ml L-leucine dehydrogenase (Sigma Inc.), and 1 u/ml NAD synthetase (Asahi Chemical Industry Co.) was prepared. Reagent solutions, each consisting of ammonium chloride 0, 250, 500, 750, 1000, 1250, 1500, 1750 and 2000 μg/dl, respectively, were prepared. 50 μl of each reagent solution were added to 1 ml of the reaction mixture. The reaction was started at 37° C.

Figure 4:
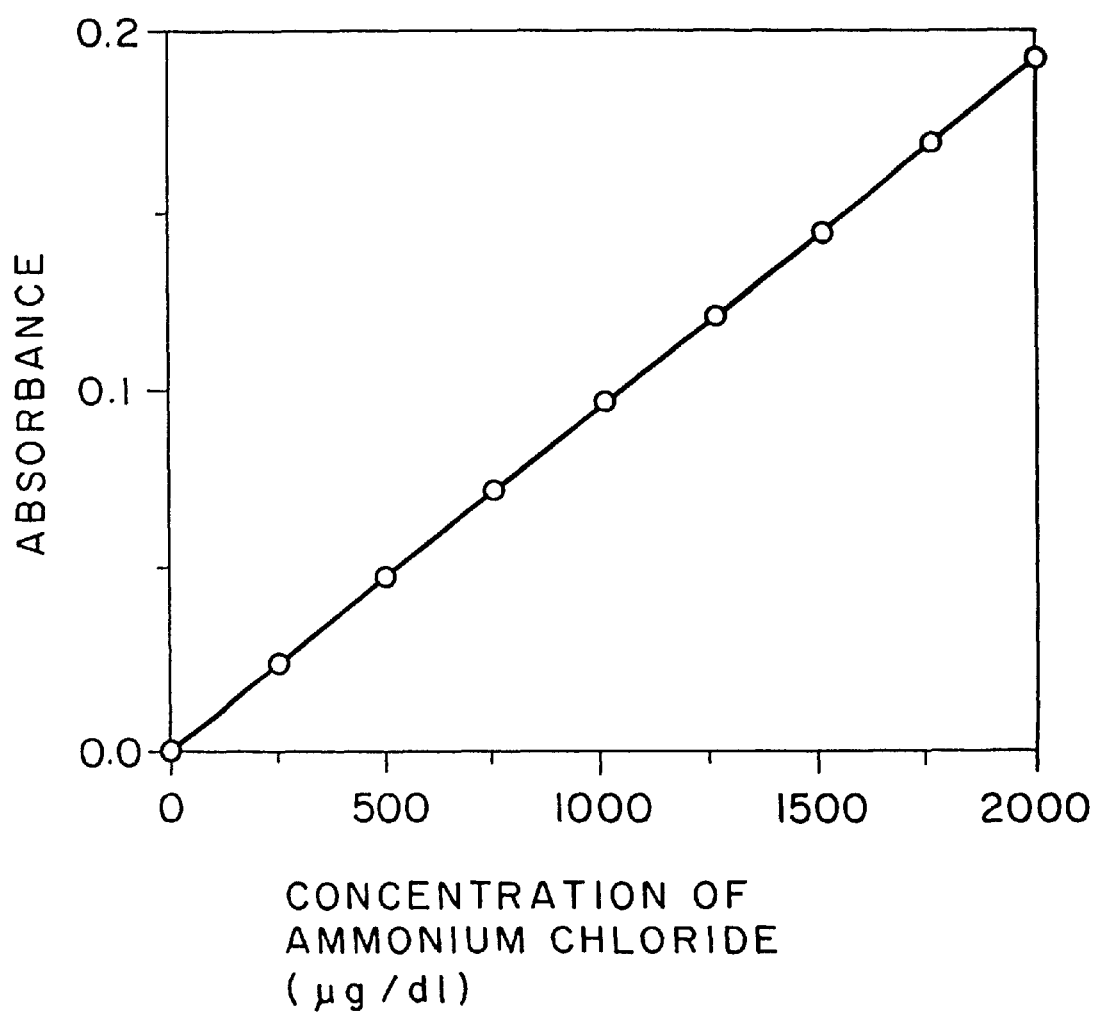
FIG. 4: A calibration curve for ammonia using assaying reagent containing L-leucine dehydrogenase.

Absorbance at 340 nm in each reaction mixture was measured for 5 minutes from 2 minutes to 7 minutes of the start by using a spectrophotometer. Result, which is detected concentration of ammonium chloride 0 as a blank, is shown in FIG. 4. As shown in FIG. 4, a quantitative assay can of up to 2000 μg/dl of ammonium chloride concentration is possible.

EXAMPLE 5

A reaction mixture containing 40 mM potassium phosphate buffer (pH 7.0), 1 mM deamidated $NAD^+$, 5 mM ATP, 5 mM magnesium chloride, 50 mM L-alanine, 50 u/ml L-alanine dehydrogenase (Asahi Chemical Industry Co.), 1 u/ml NAD synthetase (Asahi Chemical Industry Co.), 1 u/ml lactate dehydrogenase (Sigma Inc.), 1 u/ml lactate oxidase (Asahi Chemical Industry Co.), 3 u/ml peroxidase, 0.03% 4-aminoantipyrine and 0.03% TOOS was prepared. Reagent solutions, each consisting of ammonium chloride 0, 20, 40, 60, 80 and 100 μg/dl, respectively, were prepared. 30 μl of each reagent solution were added to 1 ml of the reaction mixture. The reaction was started at 37° C.

Figure 5:
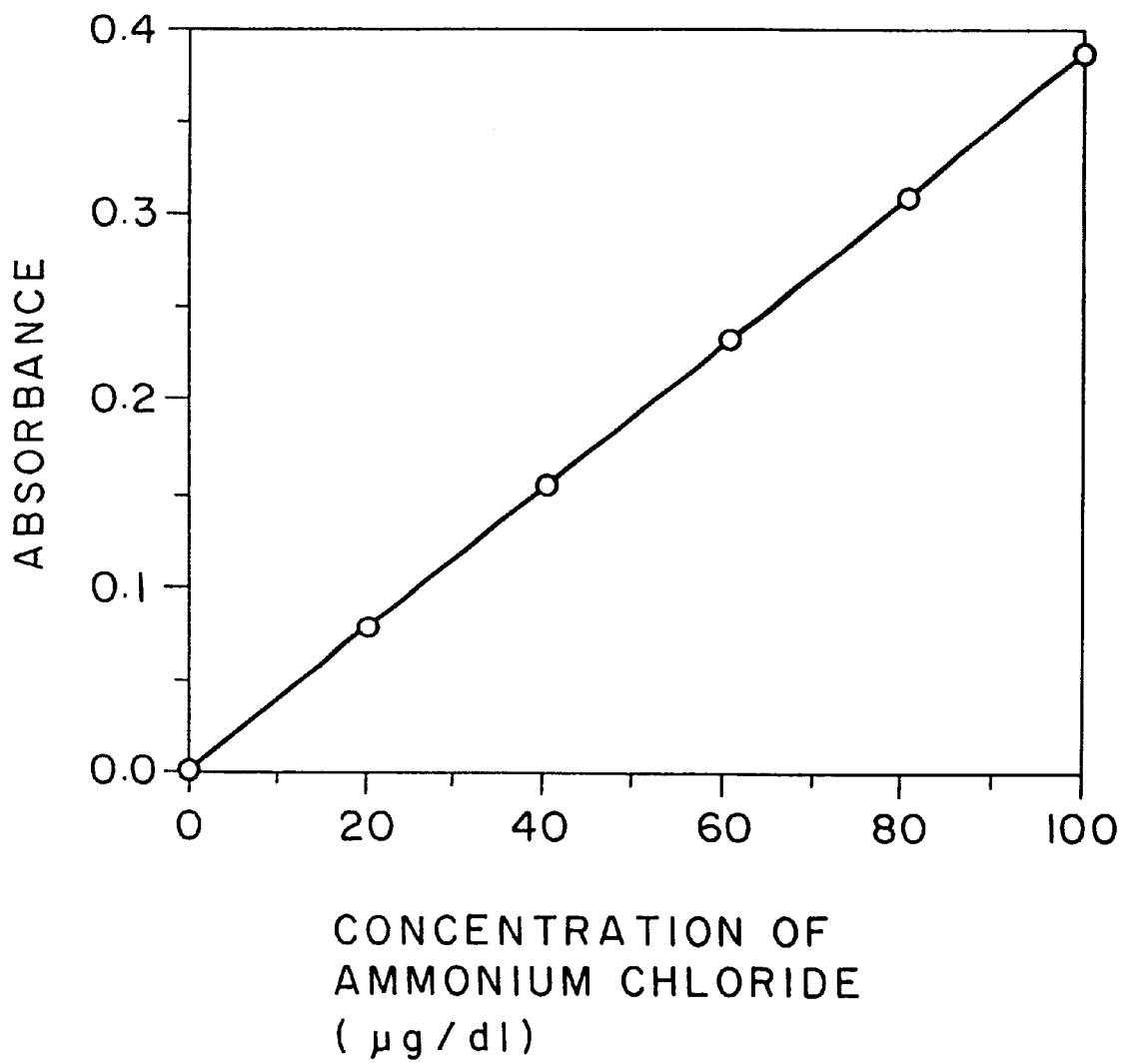
FIG. 5: A calibration curve for ammonia using assaying reagent containing L-alanine dehydrogenase, lactate dehydrogenase and lactate oxidase.

Absorbance at 555 nm in each reaction mixture was measured for 5 minutes from 2 minutes to 7 minutes of the start by using a spectrophotometer. Result, which is detected concentration of ammonium chloride 0 as a blank, is shown in FIG. 5. As shown in FIG. 5, a quantitative assay of up to 100 μg/dl of ammonium chloride concentration is possible. It could be found that even in at a concentration of 5 μg/dl, the method of the present invention had advantageous sensitivity.

EXAMPLE 6

A reaction mixture containing 40 mM potassium phosphate buffer (pH 7.0), 1 mM deamidated $NAD^+$, 5 mM ATP, 5 mM magnesium chloride, 50 mM L-alanine, 50 u/ml L-alanine dehydrogenase (Asahi Chemical Industry Co.), 1 u/ml NAD synthetase (Asahi Chemical Industry Co.) and 15 u/ml creatinine deiminase (Sigma Inc.) was prepared. Reagent solutions, each consisting of creatinine 0, 1, 2, 3, 4 and 5 mg/dl, respectively, were prepared. 50 μl of each reagent solution were added to 1 ml of the reaction mixture. The reaction was started at 37° C.

Figure 6:
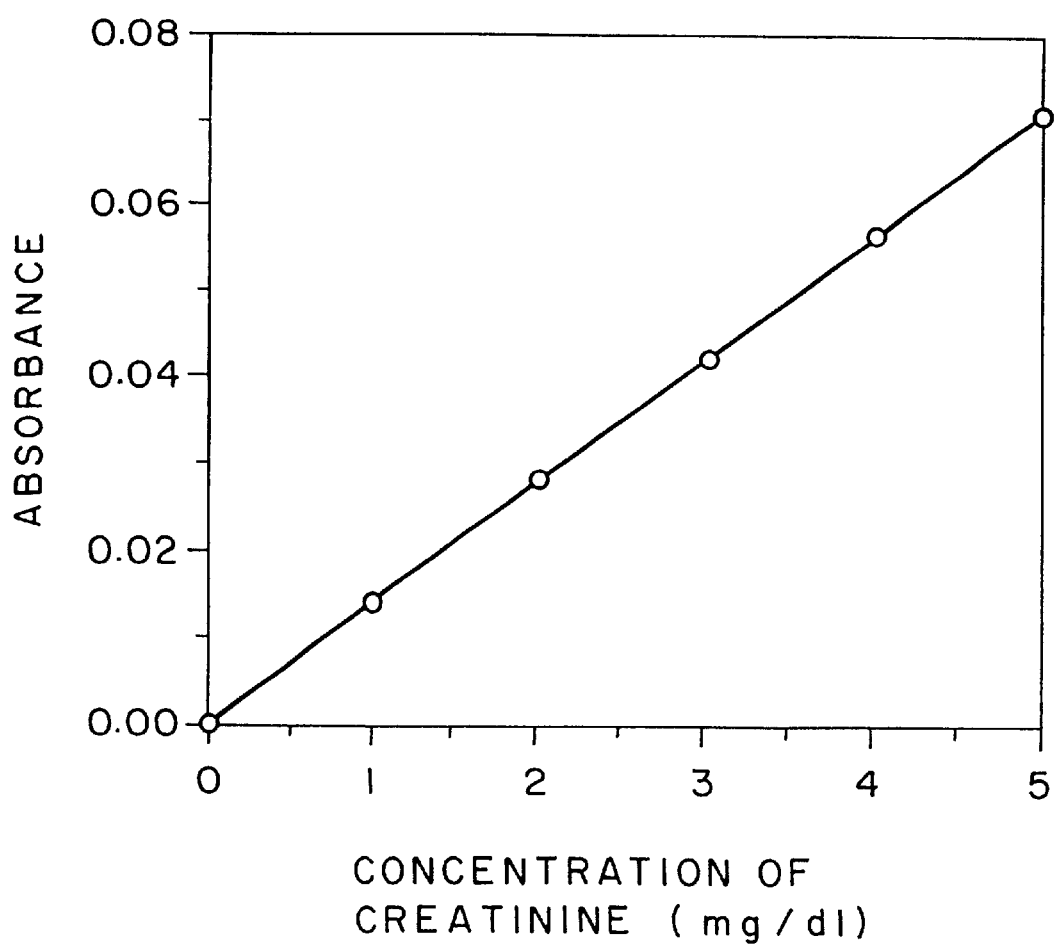
FIG. 6: A calibration curve for creatinine using assaying reagent containing L-alanine dehydrogenase and creatinine deiminase.

Absorbance at 340 nm in each reaction mixture was measured for 5 minutes from 2 minutes to 7 minutes of the start by using a spectrophotometer. Result, which is detected concentration of ammonium chloride 0 as a blank, is shown in FIG. 6. As shown in FIG. 6, a quantitative assay can of up to 5 mg/dl of creatinine concentration is possible. It could be found that even at a concentration below 1 mg/dl, the method of the present invention had advantageous sensitivity.

EXAMPLE 7

A reaction mixture containing 40 mM potassium phosphate buffer (pH 7.0), 1 mM deamidated $NAD^+$, 5 mM ATP, 5 mM magnesium chloride, 50 mM L-alanine, 50 u/ml L-alanine dehydrogenase (Asahi Chemical Industry Co.), 1 u/ml NAD synthetase (Asahi Chemical Industry Co.), 5 u/ml diaphorase (Asahi Chemical Industyrial Co.) and 0.02% nitro tetrazolium blue (Wako Pure Chemicals Inc.) was prepared. Reagent solutions, each consisting of ammonium chloride 0, 5, 10, 15, 20 and 25 μg/dl, respectively, were, prepared. 30 μl of each reagent solution were added to 1 ml of the reaction mixture. The reaction was started at 37° C.

Absorbance at 550 nm in each reaction mixture was measured for 5 minutes from 2 minutes to 7 minutes of the start by using a spectrophotometer. Result, which is detected concentration of creatinine 0 as a blank, is shown in FIG. 7.

Figure 7:
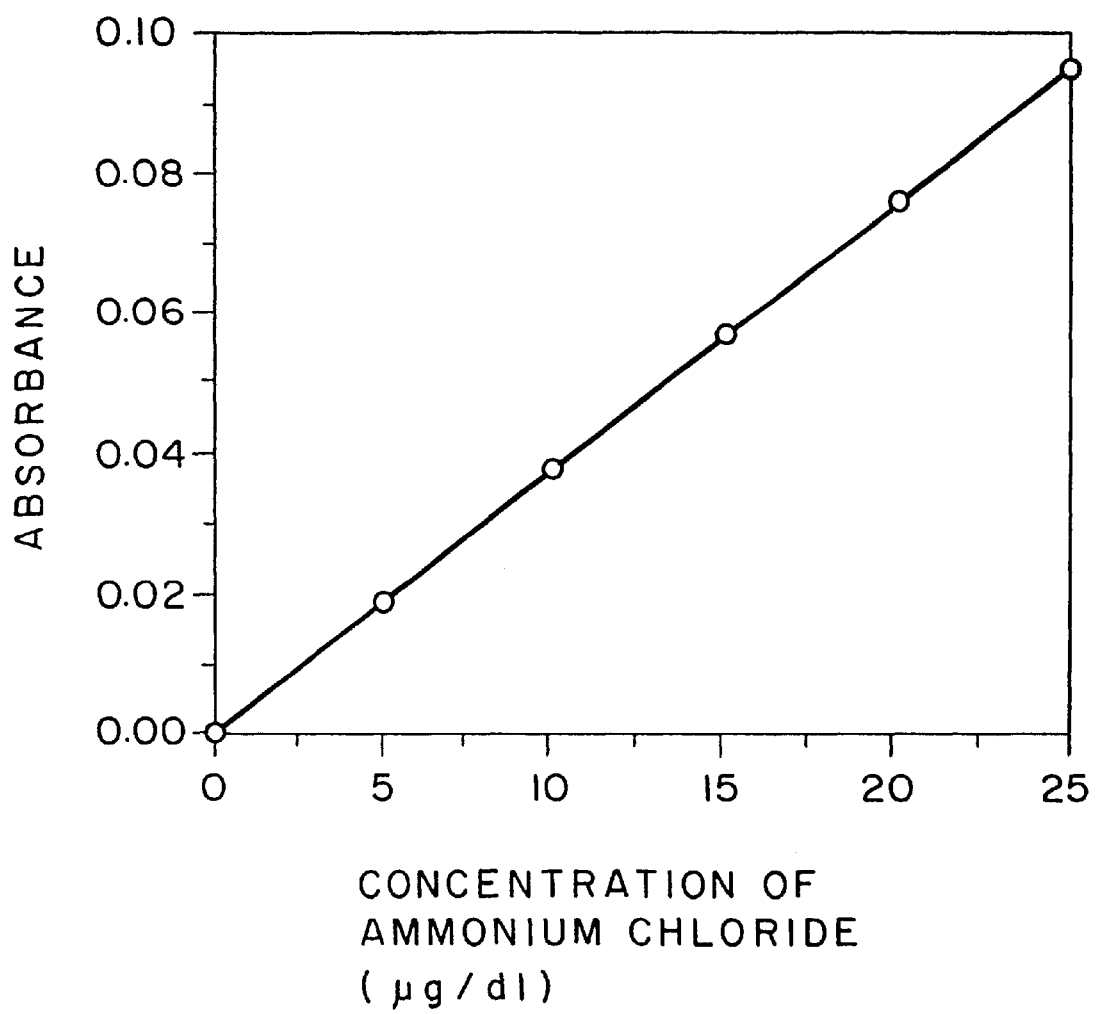
FIG. 7: A calibration curve for ammonia using assaying reagent containing L-alanine dehydrogenase.

As shown in FIG. 7, a quantitative assay is possible up to 25 μg/dl of ammonium chloride concentration. It could be found that even at a concentration below 5 μg/dl, the method of the present invention had advantageous sensitivity.

EXAMPLE 8

A reaction mixture containing 40 mM potassium phosphate buffer (pH 7.0), 1 mM deamidated $NAD^+$, 5 mM ATP, 5 mM magnesium chloride, 50 mM L-alanine, 50 u/ml L-alanine dehydrogenase (Asahi Chemical Industry Co.), 1 u/ml NAD synthetase (Asahi Chemical Industry Co.), 15 u/ml pyruvate oxidase (Asahi Chemical Industry Co.), 3 u/ml peroxidase, 0.03% 4-aminoantipyrine and 0.03% TOOS was pepared. Reagent solutions, each consisting of ammonium chloride 0, 20, 40, 60. 80 and 100 μg/dl, respectively, were prepared. 30 μl of each reagent solution were added to 1 ml of the reaction mixture. The reaction was started at 37° C.

Figure 8:
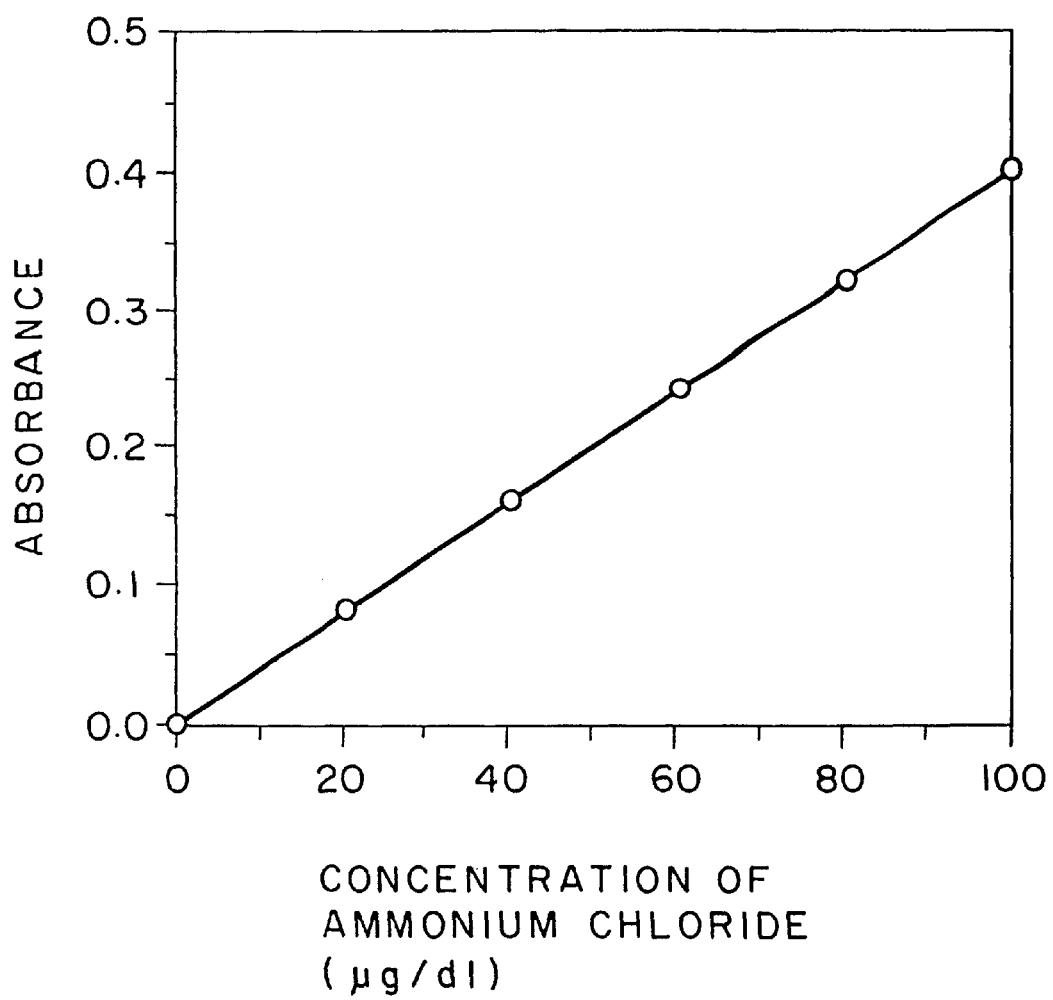
FIG. 8: A calibration curve for ammonia assaying reagent containing L-alanine dehydrogenase and pyruvate oxidase.

Absorbance at 555 nm in each reaction mixture was measured for 5 minutes from 2 minutes to 7 minutes of the start by using spectrophotometer. Result, which is detected concentration of ammonium chloride 0 as a blank, is shown in FIG. 8. As shown in FIG. 8, a quantitative assay can be is possible up to 100 μg/dl of ammonium chloride concentration. It could be found that even in at a concentration of 5 μg/dl, the method of the present invention had advantageous sensitivity.

EXAMPLE 9

L-alanine dehydrogenase and substrate L-alanine in example 1 were replaced by L-serine dehydrogenase and the substrate L-serine, L-valine dehydrogenase and the substrate L-valine, glycine dehydrogenase and the substrate glycine, L-amino acid dehydrogenase and the substrates L-alanine, L-serine, L-valine, L-leucine or L-isoleucine, respectively, and the reaction mixture was prepared in the same manner as in example 1, and the reaction proceeded in the same way as in example 1. Result indicated that test sample solution chloride can be measured by the same method.

EFFECT OF THE INVENTION

According to the present invention, high sensitivity reagents for assaying ammonia and/or ammonium ions are provided.

What is claimed is:

1. A method for assaying ammonia and/or ammonium ions in a liquid sample, said method comprising:

a) performing a main reaction comprising incubating said sample with NAD synthetase, ATP, desamido-NAD and at least one of $Mg^{2+}$ and $Mn^{2+}$ ions, thereby to generate oxidized NAD;

b) converting said oxidized NAD to reduced NAD in a secondary reaction system comprising an amine substrate and a dehydrogenase that catalyzes a reaction (i) generating ammonia molecules from said amine substrate and (ii) generating said reduced NAD from said oxidized NAD;
   wherein said ammonia molecules generated in step b) then participate in continuing said main reaction of step a), thereby to effect cycling of ammonia molecules from step b) to step a); and c) determining ammonia and/or ammonium ion content of said liquid sample from an amount of a component generated or consumed by said secondary reaction system.

2. The method according to claim 1 wherein the dehydrogenase is L-amino acids dehydrogenase, D-amino acids dehydrogenase, L-erythro-3, 5-diaminohexanoate dehydroenase (EC 1. 4. 1. 11) or 2,4-diaminopentanoate dehydrogenase (EC 1. 4. 1. 12).

3. The method according to claim 2 wherein the L-amino acids dehydrogenase is L-alanine dehydrogenase (EC 1. 4. 1. 1), L-glutamate dehydrogenase (EC 1. 4. 1. 2 and EC 1. 4. 1. 3), L-amino acid dehydrogenase (EC 1. 4. 1. 5), L-serine dehydrogenase (EC 1. 4. 1. 7), L-valine dehydrogenase (EC 1. 4. 1. 8), L-leucine dehydrogenase (EC 1. 4. 1. 9), glycine dehydrogenase (EC 1. 4. 1. 10), L-lysine dehydrogenase (EC 1. 4. 1. 15), L-tryptophane dehydrogenase (EC 1. 4. 1. 19) or L-phenylalanine dehydrogenase (EC 1. 4. 1. 20).

4. The method according to claim 1 wherein the amount of said generated reduced NAD is determined.

5. The method according to claim 1 wherein the amount of amine substrate oxidized by the dehydrogenase is determined.

6. The method according to claim 5 wherein the amount of the oxidized amine substrate is determined by measuring consumed oxygen or generated hydrogen peroxide by using oxidase which catalyzes a reaction consuming oxygen and generating hydrogen peroxide from said oxidized amine substrate.

7. The method according to claim 1 wherein the liquid sample which contains ammonia and/or ammonium ions is the ammonia and/or ammonium ions liberated or generated from creatinine.

* * * * *